(12) United States Patent
Roorda et al.

(10) Patent No.: US 8,715,719 B2
(45) Date of Patent: *May 6, 2014

(54) STABLE CHITOSAN HEMOSTATIC IMPLANT AND METHODS OF MANUFACTURE

(75) Inventors: Wouter E. Roorda, Palo Alto, CA (US); Jill A. McCoy, Evanston, IL (US); Richard Seto, San Francisco, CA (US); Eugene T. Michal, San Francisco, CA (US)

(73) Assignee: Abbott Vascular, Inc., Santa Clara, CA (US)

( * ) Notice: Subject to any disclaimer, the term of this patent is extended or adjusted under 35 U.S.C. 154(b) by 646 days.

This patent is subject to a terminal disclaimer.

(21) Appl. No.: 12/816,997

(22) Filed: Jun. 16, 2010

(65) Prior Publication Data

US 2011/0311608 A1 Dec. 22, 2011

(51) Int. Cl.
  *A61K 9/00* (2006.01)
  *A61K 9/14* (2006.01)
  *A61P 17/02* (2006.01)
  *A61K 31/722* (2006.01)

(52) U.S. Cl.
  USPC .............................. 424/443; 424/488; 514/55

(58) Field of Classification Search
  USPC ..................... 424/443, 488; 514/55
  See application file for complete search history.

(56) References Cited

U.S. PATENT DOCUMENTS

| | | | |
|---|---|---|---|
| 1,828,693 A * | 10/1931 | Deventer ........................ | 249/128 |
| 3,558,771 A | 1/1971 | Balassa | |
| 3,632,754 A | 1/1972 | Balassa | |
| 3,767,784 A | 10/1973 | Gluck | |
| 3,903,268 A | 9/1975 | Balassa | |
| 3,911,116 A | 10/1975 | Balassa | |
| 3,914,413 A | 10/1975 | Balassa | |
| 4,243,656 A | 1/1981 | Walliczek | |
| 4,265,233 A | 5/1981 | Sugitachi et al. | |
| 4,394,373 A | 7/1983 | Malette et al. | |
| 4,474,769 A | 10/1984 | Smith | |
| 4,575,519 A | 3/1986 | Kifune et al. | |
| 4,659,700 A | 4/1987 | Jackson | |
| 4,952,618 A | 8/1990 | Olsen | |
| 4,960,413 A | 10/1990 | Sagar et al. | |
| 5,116,824 A | 5/1992 | Miyata et al. | |
| 5,385,836 A | 1/1995 | Kimura et al. | |
| 5,395,305 A | 3/1995 | Koide et al. | |
| 5,597,581 A | 1/1997 | Kaessmann et al. | |
| 5,599,916 A * | 2/1997 | Dutkiewicz et al. ............ | 536/20 |
| 5,738,860 A * | 4/1998 | Schønfeldt et al. ........... | 424/402 |
| 5,830,130 A | 11/1998 | Janzen et al. | |
| 5,836,970 A | 11/1998 | Pandit | |
| 5,868,778 A | 2/1999 | Gershony et al. | |
| 5,888,987 A | 3/1999 | Haynes et al. | |
| 5,951,583 A | 9/1999 | Jensen et al. | |
| 5,957,952 A | 9/1999 | Gershony et al. | |
| 6,017,359 A | 1/2000 | Gershony et al. | |
| 6,296,658 B1 | 10/2001 | Gershony et al. | |
| 6,325,789 B1 | 12/2001 | Janzen et al. | |
| 7,041,868 B2 | 5/2006 | Greene et al. | |
| 2007/0066924 A1* | 3/2007 | Hopman et al. ................. | 602/48 |
| 2007/0113953 A1* | 5/2007 | Haywood ........................ | 156/94 |
| 2008/0014245 A1* | 1/2008 | Pacetti et al. .................. | 424/426 |
| 2008/0254125 A1* | 10/2008 | Freier ........................... | 424/488 |
| 2011/0311632 A1* | 12/2011 | Roorda et al. .................. | 424/488 |
| 2012/0269892 A1* | 10/2012 | Mossaad et al. .............. | 424/484 |

FOREIGN PATENT DOCUMENTS

| | | |
|---|---|---|
| DE | 4337152 | 5/1995 |
| EP | 0319536 | 3/1992 |
| PL | 160897 | 4/1993 |

OTHER PUBLICATIONS

Canadian Centre for Occupational Health and Safety. Thermal Comfort for Office Work. http://www.ccohs.ca/oshanswers/phys_agents/thermal_comfort.html, 2013.*
U.S. Appl. No. 12/817,005, filed Jun. 16, 2010, Roorda et al.
U.S. Appl. No. 12/817,005 filed Aug. 9, 2012, Office Action.
U.S. Appl. No. 12/817,005, filed Jun. 7, 2012, Office Action.
U.S. Appl. No. 12/817,005 filed Mar. 14, 2013, Office Action.
"Fishery Technology". vol. 11, p. 50, 1974.
"Food Biotechnology", vol. 7, p. 253, 1993.
HemCon Medical Technologies Inc., MF -024 rev. 3 2006.
HemCon Medical Technologies Inc., reprinted - vol. 60, No. 3, 2006.
USA Today, Lifesaving knowledge, innovation emerge from war's deadly violence, Mar. 27, 2006.
Effect of a Chitosan-Based Hemostatic Dressing on Blood Loss and Survival in a Model of Severe Venous Hemorrhage and Hepatic Injury in Swine, Journal of Trauma, vol. 54, No. 1, 2003.

* cited by examiner

*Primary Examiner* — Anoop Singh
*Assistant Examiner* — Anna Falkowitz
(74) *Attorney, Agent, or Firm* — Workman Nydegger; Randy Shen

(57) ABSTRACT

A method of preparing a stable chitosan hemostatic implant including preparing a lyophilizable solution of chitosan polymers and freezing the solution to obtain a frozen chitosan composition. The method further includes placing the frozen chitosan composition under vacuum so as to substantially dry the chitosan composition and curing the dried chitosan composition by first exposing it to a relative humidity and then curing the dried chitosan composition under heat so as to crosslink the chitosan polymers.

25 Claims, 5 Drawing Sheets

STABLE CHITOSAN HEMOSTATIC IMPLANT AND METHODS OF MANUFACTURE

BACKGROUND OF THE INVENTION

1. The Field of the Invention

The present invention relates to improved implantable chitosan hemostatic compositions for use in reducing blood flow or ooze in and/or from a subject with increased stability, and improved methods of manufacturing the chitosan hemostatic composition. More particularly, the present invention relates to improved chitosan hemostatic compositions and methods of manufacture that produce a flexible implant, plug, or the like that has sufficient flexibility and structural integrity to be useful in inhibiting blood flow or ooze in emergency and medical environments with increased stability.

2. The Related Technology

Blood loss is a significant cause of serious complications and even death in various situations ranging from emergencies where a subject has been shot, stabbed, or otherwise punctured through medical environments where a medical procedure does not adequately control the amount of blood flow or ooze from an incision, such as an arteriotomy. In some instances the site of blood loss can be identified and readily treated when the amount of blood flow is low. In other instances, the site or amount of blood loss may be exceedingly difficult to control and inhibit hemorrhage.

Control of bleeding can be complicated by many factors, such as lack of accessibility by conventional methods of hemostatic control, lack of ability to apply appropriate pressure or dressings, and difficulty in assessing the extent and location of injury. In some instances a medical produce can be complicated when blood continues to flow or ooze after the medical professional believes an injury or site of incision has been properly closed.

In response to the need to inhibit blood flow or oozing, various medical devices in the form of bandages, dressings, plugs, and fillings have been proposed, and such medical devices have been prepared from a variety of materials. Examples include fibrous tissues, absorbable materials, and any material that can be made into a suitable bandage. Also, hemostatic materials, such as oxidized cellulose, porcine collagen, bovine collagen, and the like have been included in medical devices to inhibit blood flow or ooze.

Additionally, chitosan, which is a derivative of the natural polysaccharide chitin, has been found to be exceptionally useful for inhibiting blood flow and ooze. The hemostatic properties of chitosan are thought to arise from the positive charge from nitrogen groups located on each monomer of the chitosan polymer which is present at physiological pH values. Also, the hemostatic characteristic of chitosan can be attributed to the cellular agglutinating property provided by the negative charges on cellular surfaces being attracted to the positive charge along the linear chitosan chain, thereby the electrostatic interaction attributing to agglutination of many cells. For example, it has been shown that chitosan is an efficient agglutinator of red blood cells, and can tip the equilibrium from flowing blood to coagulation. Studies have shown that the reduction of blood loss and survival rate of bleeding subjects is greatly reduced by using chitosan as a hemostatic dressing over traditional dressings such as cotton gauze sponges. Furthermore, the physical characteristics and lack of toxicity of chitosan bandages has been found to be superior to other hemostatic agents, such as collagen.

While chitosan has been found to be an effective hemostat, many of the hemostatic medical devices made from chitosan have suffered from the chitosan dissolving in the blood, and thereby loosing structural integrity. The lose of structural integrity of chitosan hemostatic bandages has been found to be exacerbated by high blood flow or a lengthy duration of the blood flow or ooze. In order to combat inadequate structural integrity in the presence of blood, it has been suggested to increase the amount of chitosan by preparing bandages and then compressing the bandage into a stronger configuration. However, such compression was found to cause excessive stiffness of the chitosan bandage, and cracks were intentionally introduced into the stiff, compressed chitosan bandage, which added an additional process step.

Accordingly, there is a need for an improved chitosan hemostatic composition and methods of making the same to provide a medical device that can adequately inhibit blood flow or ooze in a variety of applications.

BRIEF SUMMARY OF THE INVENTION

Generally, the present invention includes crosslinked chitosan hemostatic compositions and implantable hemostatic products as well as methods of making and using the same. The crosslinked chitosan hemostatic compositions have improved stability and can be prepared into a variety of implantable medical devices in various shapes and sizes so as to be usable for inhibiting blood flow and ooze from substantially any type of internal bleeding site. For example, the chitosan compositions can be prepared into hemostatic gauze pads, internal bandages, surgical sponges, internal incision dressings, cavity fillers, incision plugs, arteriotomy plugs, fistula plugs, sealers, sheets, rolls, combinations thereof, and the like.

In one embodiment, the present invention includes a stable chitosan hemostatic product configured for providing hemostasis to an internal bleeding site within a body of a subject. The chitosan hemostatic product includes at least the following: a matrix of chitosan polymers that are crosslinked so as to provide structural stability while in contact with blood, the matrix being substantially devoid of cracks so as to have rigidity when substantially dry; and a hygroscopic plasticizer disposed in the matrix in an amount sufficient to provide flexibility to the product when exposed to moisture. The hemostatic product can also include additional additives, such as free-radical scavengers, organic acids, multifunctional organic acids, other polymers, hemostatic agents, and the like. The chitosan hemostatic product can also be a coating that is coated onto all or a portion of a medical device. For example, the chitosan coating can be applied to a portion of a medical device that does not enter into a blood vessel. For example, the polymers can be crosslinked by up to 25% or more.

In one embodiment, the present invention includes a method of preparing a stable chitosan hemostatic product that is implantable. Such a method can include: preparing a lyophilizable solution (e.g., aqueous or acetic acid or the like) of chitosan polymers and a non-volatile plasticizer, wherein the chitosan polymers have an average molecular weight less than about 600 kD, the lyophilizable solution has a chitosan concentration of between about 2% to about 20%, and the plasticizer is lactic acid or an equally or less volatile organic acid; rapidly freezing the solution to obtain a frozen chitosan composition, wherein the cooling and/or freezing is at a rate of more than or about 1° C./minute and/or the cooling and/or freezing is conducted at a temperature of less than or about −40 degrees C.; placing the frozen chitosan composition under vacuum so as to substantially dry the chitosan composition; and curing the dried chitosan composition under heat and at a relative humidity so as to crosslink at least about 50% of the chitosan polymers, wherein the curing is performed at a temperature between about 50 degrees C. to about 130 degrees C., the curing is performed after exposing the chitosan to a relative humidity at or above about 30% relative humidity at room temperature, and the curing is performed for about 10 minutes to about 8 hours.

In one embodiment, a method of preparing a stable chitosan hemostatic product that is implantable can include: preparing a lyophilizable solution of chitosan polymers and a non-volatile plasticizer; rapidly freezing the solution to obtain a frozen chitosan composition; placing the frozen chitosan composition under vacuum so as to substantially dry the chitosan composition; and curing the dried chitosan composition under heat and at a relative humidity so as to crosslink at least about 25% of the chitosan polymers.

The method of preparing the chitosan hemostatic product can include one or more of the following: chitosan polymers have an average molecular weight less than about 600 kD; preparing the lyophilizable solution to have a chitosan concentration of between about 2% to about 20%; preparing the lyophilizable solution to have an organic acid with less volatility than acetic acid, such as lactic acid and/or a multifunctional organic acid; freezing at a rate of more than or about 1° C./minute; freezing at a temperature of less than or about −40 degrees C.; pre-evaporating the solution prior to being frozen; increasing the chitosan concentration so as to a suitable viscosity composition prior to freezing; crosslinking at least about 50% of the chitosan polymers; curing at a temperature between about 50 degrees C. to about 130 degrees C.; curing can be performed after exposing the chitosan to a humidity at or above the equivalent of about 30% relative humidity at room temperature; curing for about 10 minutes to about 8 hours; curing in an autoclave; placing the dried chitosan into a substantially gas-impermeable pouch, sealing the pouch, and curing the chitosan within the pouch; sterilizing the crosslinked chitosan hemostatic product with or without gamma radiation; preparing the hemostatic product without mechanically compressing the dried chitosan to increase density or decrease porosity; or without processing the dried chitosan in order to induce the formation of cracks or microcracks that provide flexibility when dry.

The method of preparing the chitosan hemostatic composition can also include placing a biodegradable structurally reinforcing member into the aqueous solution prior to freezing. Optionally, the method can include the following: preparing the lyophilizable solution into a tray; inserting a cutting member into the lyophilizable solution in the tray, the cutting member being configured to cut the dried chitosan composition into a plurality of chitosan hemostatic products; freeze drying the chitosan composition in the tray with the cutting member; and cutting the freeze dried chitosan composition into the plurality of chitosan hemostatic products.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
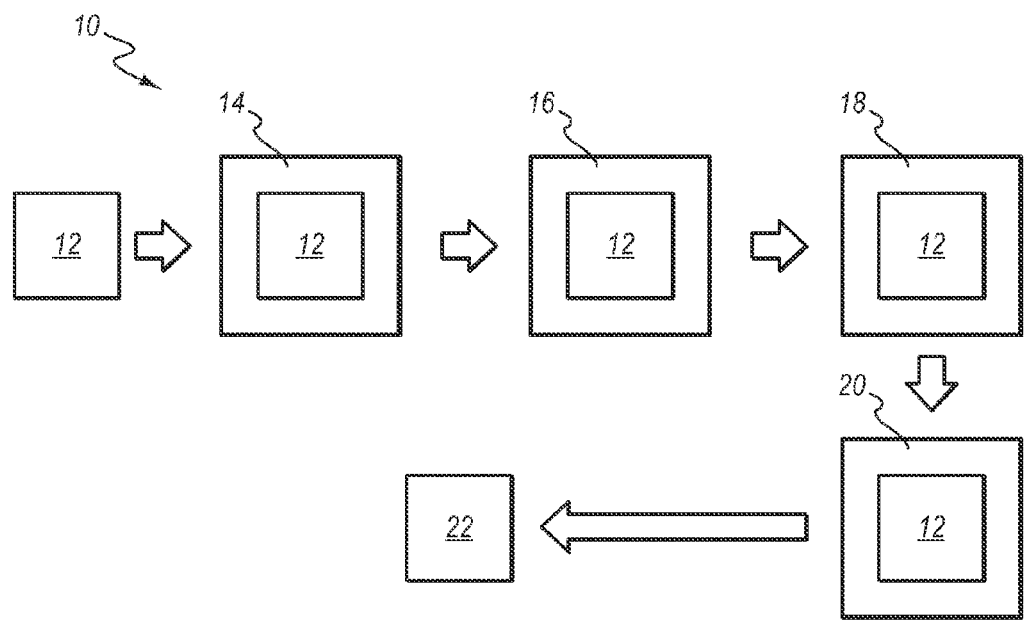
FIG. 1 is a schematic diagram that illustrates a process for preparing a stable chitosan hemostatic product in accordance with the present invention.

Generally, the present invention includes implantable chitosan hemostatic compositions and patches, plugs, and/or bandages prepared therefrom that can be used to stanch, seal, or otherwise inhibit undesirable or unnatural blood flow or ooze in a body or in a body organ, tissue, or lumen. As such, the chitosan hemostatic composition can be implanted in essentially any place or manner to inhibit blood flow or ooze and to induce agglutination of the blood components and provide for coagulation. However, the implantable chitosan hemostatic product is not configured for implantation in a blood vessel where continued blood flow is required.

Chitosan, when prepared from an acidic solution, carries positive charges on the macromolecular chain (e.g., chitosan hydrochloride, acetate, lactate etc.). These positive charges can interact with negative charges on biological systems like blood, tissue, and any think that has a positive charge. Because of this interaction, chitosan is a natural bioadhesive. This property makes it an excellent choice for a hemostatic patch or plug. The chitosan can be introduced in dry form, like a freeze dried sponge, and through interaction with the biological environment (e.g., blood, tissue, etc.) a self-adherent, hemostatic material can be formed. This type of adhesion makes chitosan a very suitable candidate for a self-anchoring arterial closure device, to be used after femoral- or other arterial access.

The implantable chitosan hemostatic composition can provide a strong clotting action so as to seal a hole, puncture, incision, or any other internal bleeding site so as to promote enhanced healing of the bleeding site and reduce opportunities for infection. In surface accessible wounds, the chitosan hemostatic composition can be inserted into the wound so as to be implanted into the underlying tissue. Additionally, the chitosan hemostatic composition can be configured to swell in the presence of blood so as to form a hemostatic barrier that plugs the internal bleeding site. The implantable chitosan hemostatic compositions, patches, plugs, and/or bandages prepared therefrom can be configured to be used internally or within or adjacent to tissue. However, it can be beneficial for the configuration of the composition to provide a hemostasis in a tissue without being introduced into a blood vessel of a subject.

I. Introduction

Chitosan is a polycationic polymer derived from chitin, which can also be used as described herein. Chitosan has a positive charge from primary amine groups that can interact with the negative charge of the lipids present on cell surfaces, such as blood cells. This electrostatic interaction has been identified as an aspect of the hemostatic properties of chitosan. Dry chitosan compositions can have increased hemostatic properties by increasing surface area, and thereby the contact area with blood. Processing methods, such as freeze drying, puffing, foaming, sponging, ballooning, combinations thereof, or the like, can be used to provide a porous, open cellular, or closed cellular structure with increased surface area. In addition to chitosan and/or chitin, other polymers having N-acetylglucosamines and N-glucosamines, such as poly-beta-1→4-N-acetylglucosamines with or without one or more monosaccharides being deacetylated and poly-beta-1→4-N-glucosamines, and derivatives thereof.

The chitosan or other similar polymer used in the present invention is preferably purified so as to be capable of use in a medical device and or used within the body of a subject. This can include being purified so as to remove proteins, other organic or inorganic contaminants. Such purification and processing of chitosan is well known in the art. Accordingly, the chitosan or other similar polymer can be considered to be biocompatible, immunoneutral, and/or generally recognized as safe for use with or within a subject, such as a human or other animal.

II. Chitosan Compositions

Chitosan can be prepared into fluidic compositions having a variety of characteristics that are suitable for being freeze dried into an implantable hemostatic product. Various characteristics of the fluidic composition can be modulated in order to provide suitable handling as well as appropriate hemostatic and structural properties. Additionally, the manufacturing process can be adapted to obtain a hemostatic product that has sufficient hemostatic and structural properties to be used as an internal patch, plug, and/or bandage.

It can be advantageous to maintain the chitosan above a minimum threshold in the product so that a high-surface area chitosan product is capable of retaining the hemostatic characteristic and to reduce the chance or propensity for bleed through of the chitosan product. Such a concentration can be identified through experimentation. Additionally, the molecular weight can be modulated to identify suitable as well as optimal molecular weights for different concentrations, which can be configured to have characteristics to avoid dissolution of the chitosan polymers when in contact with blood. For example, a plurality of different chitosan solutions at different concentrations and molecular weights, each parameter ranging from low to high and with high concentrations of low molecular weight and vice versa, can be tested for acceptable and optimum characteristics.

The process of converting chitin to chitosan can reduce the molecular weight of the chitosan product. For example, chitin can have a molecular weight well over a million, but the chitosan product the molecular weight can be significantly less. Low molecular weight is considered to be less than 200 kD, and medium molecular weight chitosan is considered to be from about 200 kD to about 500 kD. Chitosan or other polymers over about 500 kD may be considered high molecular weight. It is preferable that the hemostatic product includes polymers less than 600 kD. However, there is no defined cut-off for the effects of molecular weight on viscosity, rather there is an increase in viscosity as the molecular weight of chitosan increases.

Additionally, implantable chitosan patches, bandages, plugs, or like products of the present invention can be configured to be self-adhesive or semi-adhesive with respect to an internal bleeding site or surrounding tissue of a subject. In part, this property can be a function of the interaction of the chitosan and blood components or other body fluids as well as the interaction with the tissue. In another part, well known biocompatible adhesives can be included in order to increase the adhesive characteristic. This can allow a chitosan patch to be used internally, such as an internal hemostatic plug (e.g., intra-tract arteriotomy closure plug). Accordingly, the chitosan compositions can be formulated in substantially any shape and dimension ranging from flat pads to cylindrical plugs because the shape of the chitosan hemostatic composition can be controlled by the shape of the freeze drying apparatus or by subsequent processing and shaping.

The implantable chitosan compositions of the present invention can include linear and/or crosslinked polymers. Crosslinked chitosan polymers have an advantage in providing shape and structural integrity to the chitosan hemostatic composition, which increases strength and hemostatic efficacy. On the other hand, linear chitosan can be used at low molecular weights for increased ease in certain processing and manufacturing steps as described herein, and also for allowing for some dissolvability of the chitosan product. The low molecular weight chitosan can also be crosslinked at some point during the manufacture of a hemostatic composition to limit the amount of free chitosan polymers capable of dissolution. Thus, the present invention provides an advantage of using low molecular weight chitosan in pre-freeze drying processing and then crosslinking the chitosan during or after freeze drying to increase the mechanical and dissolution characteristics of the chitosan product.

The chitosan can be fabricated into an implantable hemostatic product in accordance with the present invention via freeze drying and optionally subsequent processing. Freeze drying is also known as lyophilization, in which a solution of chitosan is frozen and then placed under vacuum so that the solvent, such as water, sublimes from solid to vapor with minimal transition through liquid. The freezing aspect can be conducted as known for the specific solvent and modulated to take the concentration and/or molecular weight of chitosan into account. Also, any adjuvants or other components in the solution can affect the freezing aspect. It has been found, as described below, that freezing as fast as possible can be advantageous.

The implantable chitosan hemostatic composition can be prepared into a suitable form by freeze drying, which provides a sponge-like structure having increased surface area for contact with blood. The shape and size of the chitosan hemostatic product can be configured by the shape and size of the vessel containing the chitosan solution during the freeze dried process, where the product will be substantially the shape and size of the vessel or container holding the chitosan solution. However, post freeze drying processing, such as cutting and shaping can be used to shape and size the chitosan hemostatic product.

Accordingly, the chitosan hemostatic composition can be prepared into a variety of implantable medical devices in various shapes and sizes so as to be usable for inhibiting blood flow and ooze from substantially any type of internal bleeding site. For example, the chitosan hemostatic composition can be prepared into implantable gauze pads, bandages, fillers, dressings, plugs, incision plugs, arteriotomy plugs, sealers, sheets, rolls, combinations thereof, and the like.

Generally, the process for preparing the hemostatic chitosan product is modified from standard freeze drying processes in order to prepare an implantable product with increased hemostatic properties and stability. Such a general process 10 of the present invention, as shown in FIG. 1, can be performed as follows: a chitosan solution 12 is prepared that is configured for being freeze dried; the chitosan solution 12 is optionally processed 14 prior to being freeze dried; the chitosan solution 12 is then freeze dried 16; the freeze dried chitosan 12 is then processed 18 so as to crosslink the chitosan; and the chitosan 12 is processed 20 into a product for use as a hemostatic product 22 of any shape.

The chitosan can be prepared into a solution, such as an aqueous solution, that is configured for being freeze dried in order to prepare the hemostatic product. The chitosan solutions can range in characteristics depending on concentration, molecular weight, and type and amount of conditioning additives. When higher molecular weight chitosan is used, it can be advantageous to prepare dilute solutions and/or include additives that decrease the viscosity of the chitosan solution. When using lower molecular weight chitosan, it can be advantageous to prepare comparatively more concentrated solutions. Also, the acidity of the solution can be increased in a range where chitosan is not fully protonated so as to increase protonization in order to facilitate solubilization of chitosan. Traditional acidifying components, such as acetic acid or the like, can be used; however, it can be advantageous to use higher organic acids that are less volatile so that the organic acid is retained in the composition through the freeze drying process. Also, the organic acids can function as plasticizers and humectants as described in more detail below.

When using chitosan polymers, the aqueous composition can increase in viscosity as the concentration of chitosan increases. At some point, the viscosity has increased past a point where it is difficult to use. As such, preparing concentrated chitosan solutions becomes problematic, which can be exemplified by the difficulty of stirring the viscous solutions. For this reason freeze drying is often carried out from relatively dilute solutions. Consequently, the resulting sponge has a very high porosity and low solid content. In order to prevent rapid bleed-through from such sponges, the chitosan material can be increased in density by mechanical pressure applied to the chitosan prior to use as a dressing.

The chitosan compositions can be configured to overcome the viscosity problem and provide sponges of sufficient density without mechanical compression by using low molecular weight chitosan at higher concentrations in the pre-freeze drying composition. Low molecular weight chitosan can be from a solution with lower viscosity, which allows for more concentrated chitosan solutions, and thereby, more concentrated chitosan sponges after freeze drying. The cakes or sponges that result from freeze drying low molecular weight chitosan solutions may or may not have suitable mechanical strength for use as a hemostatic device, such as obtained from medium to high molecular weight chitosan. However, the mechanical strength of low molecular weight chitosan cakes or sponges can be increased by including a biodegradable structurally reinforcing webbing, backing, mesh, or other similar materials in the composition during the freeze drying process. Additionally, other beneficial agents, such as plasticizers, adjuvants, excipients, pharmaceuticals, and the like can still be included in the chitosan composition with the biodegradable webbing. Also, the freeze-dried chitosan composition with or without webbing can be cured by being heated in the presence of water so as to crosslink the chitosan polymers together, which structurally reinforces the chitosan product.

The chitosan hemostatic composition of the present invention can have improved mechanical and dissolution properties when the freeze drying process is performed with high molecular weight chitosan or more concentrated chitosan solutions. However, fluid chitosan compositions with low molecular weight chitosan or at low concentrations are easier to work with compared to high molecular weight chitosan or concentrated solutions. It has been found that the use of low molecular weight chitosans or low concentration chitosan solutions that are freeze dried can result in hemostatic compositions that have decreased effectiveness. Such decreased effectiveness can be counteracted by modulating the chitosan composition and process for preparing the hemostatic product so as to have structural integrity for increased effectiveness, durability, and hemostatic potential. The chitosan compositions and processes can be modulated so as to utilize low molecular weight chitosan and/or dilute solutions, and then increase the concentration by pre-evaporation prior to being freeze dried. Another Additionally, techniques have been explored to effectively increase the structural integrity of a chitosan plug after the freeze drying so that the chitosan hemostatic composition functions similarly to compositions that are prepared with higher initial chitosan molecular weights concentrations. Pre-evaporation, and/or post-freeze dry curing and/or crosslinking can be used to increase the effectiveness and hemostatic potential similar to compositions having increased concentrations of chitosan. Such processing techniques can provide increased hemostatic properties by having more chitosan available to interact with the blood. Thus, low molecular weight and low concentration chitosan solutions can be utilized in the process for preparing the hemostatic product to ease handling, and can be processed so as to increase the hemostatic potential.

In one embodiment, the present invention includes preparing chitosan solutions of lower molecular weight chitosan polymers. The concentrations can be widely varied depending on the molecular weight of chitosan as well as the processing conditions and techniques. The concentrations of chitosan can be evaluated based on the molecular weight, handling viscosity, and the targeted chitosan concentration of the freeze dried product.

Figure 2:
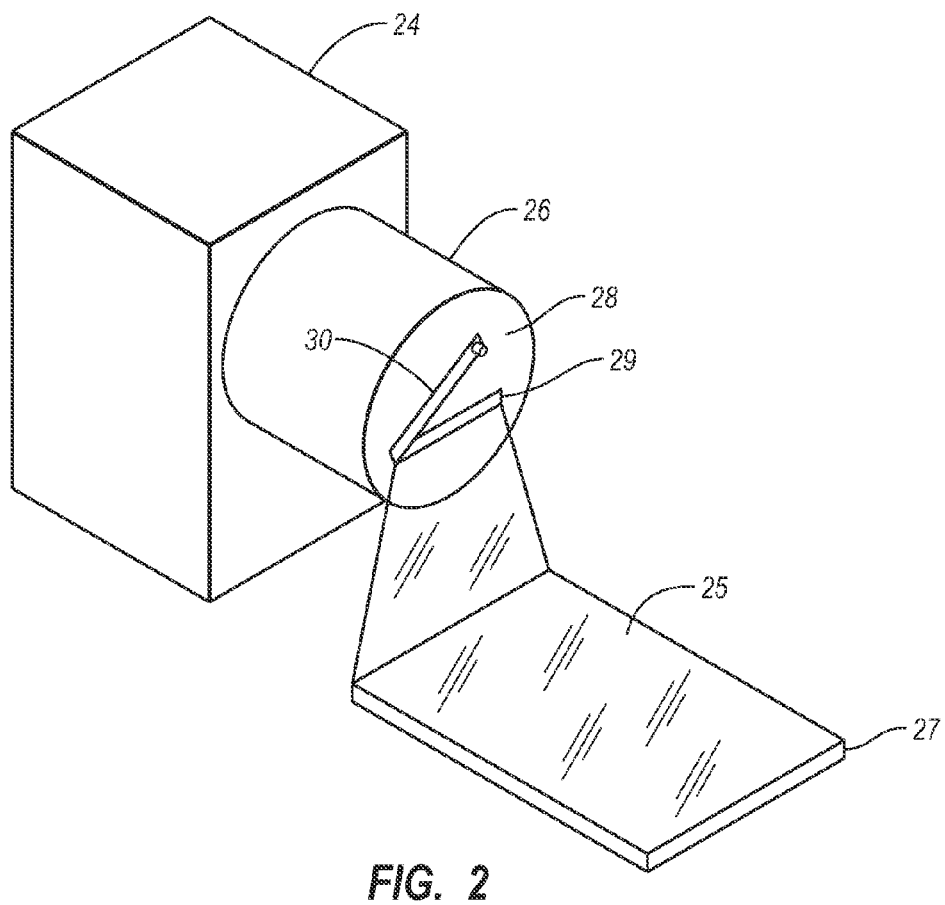
FIG. 2 is a schematic representation of an embodiment of a dispensing system for dispersing a chitosan composition into a thin film.

As shown in FIG. 2, a chitosan composition can be prepared in a mixer 24 cast into a thin film 25 from a chitosan solution, which can range from dilute to concentrated and viscous as described herein. The thin film can be from about 0.1 mm to about 10 mm, preferably from about 0.25 mm to about 7.5 mm, more preferably from about 0.5 mm to about 5 mm, and most preferably from about 1 mm to about 2 mm. The film 25 can be cast by using a dispenser 26 to dispense the chitosan solution into a tray 27 having appropriate dimensions. The dispenser can be fluidly coupled to a reservoir (e.g., mixer 24) having the chitosan solution and to a mouthpiece 28 from which the chitosan solution is dispensed. The dispenser 26 can be configured to vary the flow rate and amount being dispensed as desired. Optionally, the mouthpiece 28 can have a calibrated slit 29 or other shaped orifice through which the chitosan solution is dispensed into the tray. For example, the mouthpiece 28 can be dimensioned similarly as the dimension of the tray 27. The reservoir can be filled with the chitosan solution, and the solution is fed by gravity, pressure, positive displacement, or the like through the mouthpiece 28 and onto the tray 27 at a height determined by the desired thickness of the film 25. The mouthpiece 28 can be mounted on the tray 27 in a manner that allows for the mouthpiece 28 to slide over the length of the tray 27 while dispensing the chitosan solution. Optionally, the mouthpiece 28 can include a wiper 30 that wipes the film 25 to the desired thickness. If desirable, the mouthpiece 28 can be separated or decouplable from the tray 27 and/or wiper 30. Also, the wiper 30 can include components for functioning as a wiper 30, such as components in a standard windshield wiper.

Figure 6:
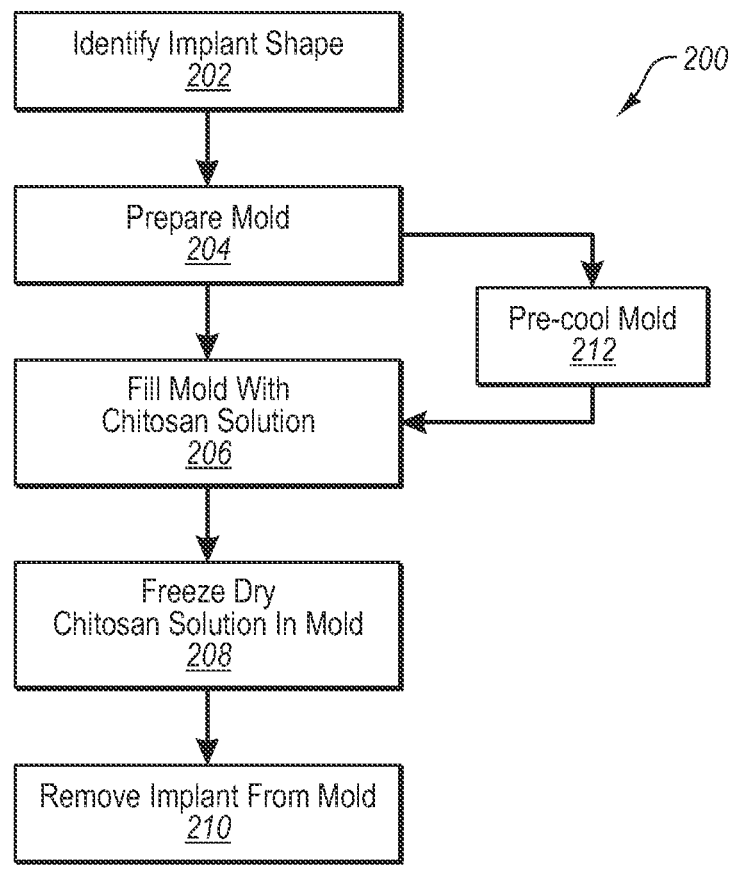
FIG. 6 illustrates a method for manufacturing an implant.

FIG. 6 shows that a process 200 for preparing an implant can include: identifying implant shape 202; prepare a mold for the shape 204; fill the mold with chitosan solution 206; freeze dry chitosan solution while inside the mold 208; removing implant from the mold 210. Optionally, the process 200 can include pre-cooling the mold prior to receiving the chitosan solution 212, such as a temperature sufficiently low to induce flash-freezing of the solution.

In some cases, cylindrical shaped implants may be desirable, like in the case of puncture wounds or access sites for minimally invasive or percutaneous procedures. For example, a mold can be prepared by drilling holes through a block of a non-adhesive material, like PTFE. Also, a metal block can be coated with a non-stick surface after the holes are drilled for use as a mold. The holes are about the size of the desired implants. A bottom plate can be attached to one side of the block, and the holes are filled with the chitosan solution to be freeze dried. It can be advantageous to pre-cool the block to a low enough temperature to induce immediate flash-freezing of the solution. The block is placed in a freeze dryer, and the solutions are dried. After drying the chitosan compositions the bottom plate can be removed, and the chitosan composition pushed out of the holes.

In one embodiment, the hemostatic efficacy can be increased by increasing the amount of chitosan in a hemostatic chitosan plug. The hemostatic efficacy of the chitosan plug increases with an increase in the concentration of chitosan. However, at a certain concentration level, a chitosan solution can become overly viscous. Also, increased amount of chitosan in the hemostatic plug can cause the plug to be stiffer than needed or desired. An overly stiff plug may not be properly configured for implantation as needed or desired. Also, an overly stiff plug or tissue filler may be uncomfortable which can be an irritant to the patient. It has now been found that such stiffness from increased chitosan in the plug can be overcome by including components that promote flexibility. Such components can include plasticizers, water, elastomers, humectants, polysaccharides, sugars, hygroscopic salts, glycerols, polyols, polyethyleneglycols, combinations thereof, and the like.

The use of plasticizers can be advantageous in providing for increased flexibility by plasticizing the chitosan hemostatic composition. Additionally, hygroscopic plasticizers can be utilized as indirect plasticizers by increasing the amount of water retained within or absorbed into the chitosan hemostatic composition, where the water associated with the plasticizer functions to soften and ultimately increase flexibility. Such flexibility can be maintained in the aqueous internal environment of a living body. The water attracted to the hygroscopic plasticizer can cause the plug to swell prior or during use so as to increase the flexibility. Accordingly, the flexibility of the chitosan hemostatic composition can be increased by the hygroscopic plasticizer that attracts an amount of water and the water provides further flexibility. The control of the amount of plasticizer and thereby the amount of water can be used to control the flexibility of the chitosan hemostatic composition. Such increase in flexibility provided by the hygroscopic plasticizer and water combination can be characterized as the chitosan hemostatic composition being flexible when wet or in the presence of moisture. On the other hand (e.g., when dry), the chitosan hemostatic composition that has substantially all of the water removed is substantially more rigid. Thus, the chitosan hemostatic composition is more rigid and stiff when dry. When dry, subsequent rehydration by exposure to moisture can again provide the increase in flexibility and thereby comfort to the user.

The plasticizer, such as PEG, can be included in the chitosan hemostatic composition and resulting product, such as a plug, in an amount ranging from about 10% to about 50% by weight of the chitosan product, whether in an implant, plug, or other hemostatic form, more preferably from about 20% to about 40% by weight of the chitosan product is plasticizer, and most preferably about 30% by weight is plasticizer. The percentages can be based on the indirect plasticizer without water or the plasticizer with water because water also functions as a plasticizer to provide functionality. However, the ranges and types of placticizer can be modulated depending on the molecular weight of chitosan, concentration of the fluid chitosan solution, and the degree of crosslinking, as well as the type of chitosan product. Thus, an effective amount of plasticizer can be used so as to provide a suitable chitosan composition for processing into a hemostatic product as described herein.

Additionally, multifunctional organic acids that have the capability to form complexes with more than one polymer chain of chitosan can be utilized to effectively crosslink the chitosan polymer chains together. Such crosslinking with multifunctional acids, such as organic acids, can be used to substantially reduce the dissolution rate of the chitosan hemostatic composition when exposed to blood. Examples of such multifunctional acids include polyanionic molecules such as polyacrylic acid, proteins, collagen, organic acids, citric acids, and the like. The use of such multifunctional acids may crosslink the chitosan prior to and/or after freeze drying, and in some instances may crosslink the chitosan to inhibit solubilization. As such, the chitosan can be solubilized in solution with an acid, such as lactic acid, and then crosslinked with the multifunctional acid prior to lyophilization. Also, the multifunctional acid can be introduced into the freeze dried chitosan composition under conditions suitable for crosslinking, such as the multifunctional acid being in the present of sufficient water.

Additionally, it has now been found that select non-volatile organic acids can be included in a chitosan composition. Using a non-volatile acid can increase protonation after freeze drying, but since evaporation happens during freeze drying the non-volatile acid does not have an effect on the solubility before freeze drying. Previously, acidic counterions, such as hydrochloric acid or acetic acid, have been used to acidify a composition so as to promote chitosan solubility. However, such acidic counterions are susceptible to volatilization during freeze drying, which may cause formulation control problems. The use of less-volatile or non-volatile organic acids can provide the benefit of increased protonation of chitosan. Lactic acid, citric acid, and other similar acids or higher organic acids can be used for acidification and protonation. Examples of organic acids can include pyruvic acid, glycolic acid, hydroxy-butyric acid, maleic acid, fumaric acid, and other organic acids with water-solubility enhancing functional groups. Additionally, non-water soluble acids can be used if the solvent is changed from pure water to a mixture of water and an organic solvent, like ethanol, methanol or acetone, as long as freezing temperatures are employed that are low enough to overcome the freezing-point lowering effects of the organic solvents. Use of surfactants is another option. The selection of a suitable solvent system allows for the use of a wide range of arganic acids. The exact composition of each mix will depend on the requirements of the specific formulation, experimentation by someone skilled in the art of formulation can determine suitable combinations of acids and solvents.

Additionally, some higher organic acids, such as lactic acid, can have a dual purpose by also functioning as a plasticizer. The use of plasticizers in chitosan compositions of the present invention is described in more detail herein. Moreover, lactic acid can be a non-irritating counterion, which promotes patient compliance by reducing irritations associated with plugs, and thereby increases use.

While counterions, such as obtained from acetic acid, can be used to promote solubility and flexibility, it has been found that acetic acid is likely to evaporate during the formation of the chitosan hemostatic composition during freeze drying or pre-evaporation techniques. As such, lactic acid and other similar or high organic acids can be advantageous by being less susceptible to evaporation. Less evaporation during processing can retain more of the counterion in the composition to provide the characteristics described herein, such as increase flexibility by the counterion being a plasticizer. Lactates can be especially advantageous for increasing the flexibility of a hemostatic chitosan product.

Lactic acid and other similar organic acids can be utilized advantageously as adjuvants for the chitosan hemostatic composition. The use of lactic acid can provide a chitosan hemostatic composition in an internal patch, bandage, plug, or the like that is softer, allows for more control over the manufacture process and end product, is biocompatible, and provides a favorable pH.

In one embodiment, the chitosan composition can include free radical scavengers in an amount and disposition sufficient for inhibiting radiation-induced degradation of the chitosan polymers into shorter polymers. Chitosan is radiation sensitive and can degrade under exposure to radiation, such as the radiation of gamma sterilization. As such, the plugs of the present invention can be configured to inhibit such degradation from radiation by including free radical scavengers, such as sodium metabisulfite (e.g., from about 0.01% to about 1%), sodium ascorbate (e.g., about 0.01% to about 1%), tertiary-butylhydroquinone (TBHQ) (e.g., up to about 0.02%), or propylgallate (e.g., up to about 0.1%). However, other free radical scavengers can be employed. Additionally, the molecular weight of the chitosan can be used at an initial weight and configured to account for degradation such that the chitosan has the desired molecular weight after sterilization. Also, curing and crosslinking can be used to overcome issues of degradation, such as when the chitosan is initially a medium or low molecular weight chitosan.

In one embodiment, the chitosan can be combined with another material having different properties such that the combination of chitosan and the other material provides an improved hemostatic composition. This can include an internal patch or plug prepared with a different polymer, which can have superior characteristics in mechanical strength, reduced solubility, reduced or increased bioabsorption, flexibility, shape memory, or the like. The chitosan can be commingled with the other material as well as coated thereon. For example, chitosan can be dissolved in an acidic solution and then sprayed, dipped, or otherwise deposited onto a freeze dried implantable patch or plug having absorptive, sponge, or flexible characteristics, which then imparts the hemostatic and adhesive characteristics of chitosan thereto. Examples of the other material can include hyaluronic acid, albumin, alginate, a sponge, polyurethanes, medical grade polymers, and the like.

In addition, the chitosan can be dissolved in an acidic aqueous solution, and this solution can be sprayed or dipped onto a freeze-dried plug made of another material. The other material can be fabric, polymeric, foam, high density foam, cross-linked, or processed or formulated as described herein with a chitosan or other polymer.

Also, a webbing can be combined with the chitosan to provide enhanced structural properties. A webbing of some form of fibrous material or fabric can be used to reinforce the chitosan formulation. For implantable materials, a biodegradable webbing is preferred. Suitable materials include the hydroxyalkanoic acids, like lactic, glycolic and hydroxybutyric acid, polycaprolactone, polyphosphazenes, polyanhydrides, tyrosine carbonates, biodegradable polyurethanes and biodegradable acrylic polymers. Cross-linked, biodegradable forms of polymers like gelatin, collagen, PEG and the like may also be suitable. For extractable devices any type of flexible, biocompatible fibrous material or fabric can be used, including polyacrylics, poly-urethanes, poly-olefines and poly-esters.

In cases where the desired concentration of chitosan in the formulation is so high that processing the solution prior to freeze drying becomes impractical, a pre-evaporation step can be used. The hemostatic efficacy of the chitosan composition can be increased by increasing the density of the chitosan by a pre-evaporation process that increases the concentration of chitosan prior to the freezing process of freeze drying. The pre-evaporation process can be performed with dilute solutions of low, medium, or high molecular weight chitosan. Also, it can be performed when regular or already concentrated solutions of chitosan having an appropriate molecular weight for retaining some solubility and/or suspension of the chitosan prior to the pre-evaporation. While complete or substantially complete evaporation may result in a dense, non-porous structure, such complete evaporation can be used in some instances, especially when another method is used to provide the porosity and increased surface area, such as supercritical fluid gassing. However, substantially porosity can be provided by also using pre-evaporation when a sufficient amount of water is retained in the chitosan during the freezing process. As such, the amount of porosity of a pre-evaporated chitosan can be controlled by controlling the amount of residual water remaining after pre-evaporation. The pre-evaporation can be performed by any method to passively or actively evaporate water from the chitosan composition. For example, the chitosan composition can be passed through an oven, such as a tunnel oven, to pre-evaporate some of the water. Also, heated air can be passed over or directed onto the chitosan composition. Additionally, the chitosan solution can be exposed to reduced pressures or vacuum conditions prior to the freeze drying process. The pre-evaporation can be combined with any other process descried herein.

For example, a low molecular weight chitosan solution (Mw<100,000 D) can be mixed with a simple impeller or even a magnetic stirrer at a concentration of 2%. The solution can be formed into shapes by simply pouring into molds. The molds can be of any shape for lyophilization, such as spherical, square cross-section, rectangle cross-section, triangle cross-section, polygonal cross-section of various, or the like. Once the solution is in the molds, the volume can be reduced by evaporation of solvent, such as water, to the desired concentration. For instance, to obtain a freeze dried cake of sufficient strength, the solution can be pre-evaporated or dried down to a 10% concentration. At this concentration the solution would be too viscous to process with a simple impeller or stir bar. Other conditions can easily be determined by one skilled in the art. For instance, if a high viscosity mixer with self-wiping and wall-scraping blades is available, the starting solution may have a much higher viscosity. This could translate into a higher initial viscosity of the chitosan, into a higher molecular weight, or a combination of both. As a rule of thumb, an evaporation of 10% of the initial volume may have a noticeable effect, but more typically at least a 50% reduction in volume would result in changes of practical significance. Reductions by more than 90% are possible, but may be impractical from a process-economic perspective.

In one embodiment, the chitosan composition can be degassed prior to being processed. The degassing of the chitosan before processing can allow for more accurate control of the characteristics, such as porosity, of the chitosan cake or sponge that is produced. The degassing can be accomplished by application of vacuum, ultrasonication, heating, or the like. Also, the degassing can be conducted at a controlled temperature that is held constant or variable.

In one embodiment, the chitosan composition can be processed into a dense film and then swollen prior to lyophilization. As such, the pre-evaporation or other process can be used to process the chitosan into a dense film. The dense film is then swollen with an aqueous solution which utilizes the hydrophilic properties of chitosan to attract the water. While the dense film is swollen, it is not solubilized or suspended in the aqueous solution, but does take up water to increase the overall volume. For example, aqueous liquids and/or high humidity can be used for the swelling of the film, which decreases the density of the film. Also, supercritical solvents can be used with the dense film in order to provide a foamed film. The swollen or foamed film can then be processed with lyphilization and other processes as described herein to obtain a hemostatic product.

In one embodiment, the pre-evaporation can be conducted so as to produce a higher concentration of chitosan and higher viscosity. This can include evaporating from about 25% to about 90%, from about 40% to about 80%, or from about 50% to about 80% of the initial volume, depending on the desired product.

In one embodiment, the pre-evaporation can be conducted so as to produce a lower concentration of chitosan and lower viscosity. This can include evaporating from about 5% to about 50%, from about 10% to about 40%, or from about 15% to about 30%) of the initial volume, depending on the desired product.

In one embodiment, the hemostatic efficacy can be increased by modulating the process of freeze drying a chitosan solution. Chitosan plugs are typically utilized in a dry form so as to maximize the hemostatic potential by excluding moisture. Oven-drying chitosan can provide a dry sheet that can be used as a hemostatic plug, where the sheets can be dense with low surface area. On the other hand, freeze drying can be used to increase surface area and provide porous plugs or sponges. Previously, it has been reported that slow freezing in a freeze drying process is advantageous to introduce uniform pores into chitosan and to avoid brittleness and a propensity for forming cracks (U.S. 20070083137, which is incorporated herein by specific reference). Contrarily, it has now been found that fast freeze drying may be more advantageous in preparing a chitosan plug having superior hemostatic and/or other properties. In part, fast freezing can provide more pores that may be smaller, which together can increase the hemostatic efficacy. The pores can result from ice crystals subliming during the freeze drying process. In part, it is thought that fast or flash freeze drying can provide a large number of small ice crystals rather than unfavorable large ice crystals. This includes a fast rate of cooling and/or freezing, such as the fastest possible rate of cooling and/or freezing through about 0.5° C./minute. If flash freezing is not feasible, An optimum freezing rate can be determined for chitosan compositions having different components, amounts, or other characteristics. For example, the cooling and/or freezing rate can be about 1° C./minute to about 20° C./minute, in another configuration from about 2.5° C./minute to about 15° C./minute, and in yet another configuration from about 5° C./minute to about 10° C./minute. Flash freezing is most advantageous. The maximum or optimum freezing rate may be determined by the capacity of the freezing apparatus, system, or method being utilized. Thus, a large number of pores can be formed during the evaporation phase when a large number of ice crystals are sublimed.

The freezing can be conducted by any process for freezing a chitosan solution, especially an aqueous chitosan solution. This can include tunnel freezers, batch freezers, flash freezers, and the like. A representative temperature which the chitosan solution is subjected for freezing is about −60 degrees C., but can be less than about 0 degrees C., more preferably less than −20 degrees C., even more preferably less than −40 degrees C., and most preferably less than −60 degrees C. Temperatures less than −80 degrees C. can flash freeze the chitosan solution depending on the characteristics of the solution. However, the temperature can be any temperature below the glass transition temperature (Tg). Additionally the temperature can be about 0° C. or above 0° C. when the sublimation occurs at a fast-enough rate.

Freezing at temperatures that induce flash freezing is most effective. Under flash freezing conditions the solution is cooled below its freezing temperature, so that once freezing starts, the formed ice crystals act as seeding crystals, and very rapid (flash) freezing follows. The ice crystals formed in this way tend to be very small, causing the formation of a cake with a large number of small pores and a very high surface area after drying. The conditions for flash freezing depend on sample size and configuration, but typically involve temperatures below −40 C. The optimal temperature during the freezing process is entirely product dependent, and drying cycle optimization is a routine part of any commercial freeze drying process development The vacuum aspect of the freeze drying can be any reduced pressure less than atmospheric or ambient conditions. The vacuum can be the highest vacuum possible. The vacuum can be modulated so as to alter the sublimation rate.

In one embodiment, the structural functionality of a chitosan plug prepared via fast freeze drying can be improved by including a plasticizer. Substantially any plasticizer known for plasticizing polymers for use in medical applications can be included in the chitosan composition. The use of a plasticizer in fast freeze drying can produce a chitosan plug that has increased hemostatic efficacy. Also, the plasticizer can provide a chitosan plug with more flexibility and thereby less propensity to form cracks before or during use. Also, the combination of fast freeze drying and a plasticizer can provide for an increase in flexibility, which combined increases the hemostatic efficacy and functionality by increasing comfort and thereby patient compliance.

The freeze dried product can be an amorphous sponge that retains some water. The water can be useful in later processing steps, such as curing and crosslinking.

A lower molecular weight chitosan composition can be prepared as a more concentrated solution and then processed through at least one freeze drying procedure. The chitosan can then be processed so as to render the chitosan significantly less soluble through insoluble. Crosslinking is an example of a process to reduce the solubility of a lower molecular weight chitosan, which effectively produces higher molecular weight macro structures. Crosslinking of chitosan has been found to increase stability during gamma radiation and exposure to fluids such as blood. The crosslinked chitosan has fewer chitosan polymers that are capable of degrading from the hemostatic composition and entering the blood stream. The crosslinking can be accomplished using standard crosslinking reagents capable of reacting with moieties on different chitosan polymer chains. Such crosslinking can be performed before or after freeze drying. However, it can be advantageous to crosslink the chitosan after being freeze dried.

Also, a curing process can cause the chitosan to crosslink with itself without a traditional crosslinker to extend between chitosan polymer chains. For example, curing can be conducted by heating the freeze dried chitosan composition in the presence of water, which can be a vapor, moisture, or available from hydroscopic entities (e.g., humectants, plasticizers, PEG, and the like) present in the composition. In any event, insolubilizing the chitosan through crosslinking can provide a hemostatic composition without problems associated with the chitosan solubilizing in the blood. Also, an uncrosslinked chitosan composition can be cast or otherwise processed as described herein and then cured by heating in the presence of water. This can produce a chitosan hydrogel rather than a chitosan solution when introduced to the same amount of water or other aqueous liquid such as blood.

The curing process can rehydrate the chitosan and induce a crosslinking reaction that links different chitosan polymers with each other. The conditions for curing can range depending on the desired characteristics of the hemostatic product. In one example, a low molecular weight chitosan is prepared into a solution, freeze dried, and then heated in the presence of water vapor to about 70 degrees C. to about 90 degrees C. for about 1 hour so as to cure and crosslink the chitosan. Such curing can involve a brownish coloring of the chitosan which is similar to a brown crust, and in those cases the brown color may be an indication of curing and crosslinking. This produces a chitosan composition have macro structures of crosslinked chitosan with high molecular weights. The curing process can be controlled to crosslink any percentage of chitosan polymers. This can include from 50% to about 75% of chitosan polymers being crosslinked; however, the crosslinking percentage can be increased or decreased as desired or needed for a particular product by modulating the curing process. The cured chitosan hemostatic composition can be characterized by being rigid and/or brittle when dry, and then more flexible when rehydrated or wet as described herein.

The chitosan hemostatic product can have any degree of crosslinking that stabilizes the mechanical and dissolution characteristics of the chitosan. However, crosslinking of over about 25% of chitosan polymers can be advantageous. This includes crosslinking from about 25% to 100% of chitosan polymers, in another configuration from about 30% to about 90%, in yet another configuration from about 40% to about 80%, in still another configuration between about 50% to about 75% chitosan polymers being crosslinked, and in still yet another configuration between about 60% to about 70% crosslinking or even 70% to 80% crosslinking. An example can be above about 60% crosslinking. When 50% of the chitosan polymers are crosslinked, less than or about 50% of the chitosan polymers are available for dissolution; however, other molecular interactions and chitosan interactions with blood components further reduce the amount of chitosan polymers that can be separated from the hemostatic composition when contacted with blood.

In one embodiment, the curing procedure can be conducted in an autoclave. The autoclave curing process can be performed in any manner in which an autoclave operates. The freeze dried chitosan is placed into the autoclave and set to run for a desired duration to produce the desired amount of crosslinking. The settings of the autoclave can be set in a manner dependent on the characteristics of the freeze dried chitosan in order to control the curing reaction and thereby controlling the crosslinking. This offers a wide range of conditions for curing, and optimal conditions can be determined by routine experimentation by analyzing the crosslinking percentage. For example, the autoclave can be set to a temperature at or above 90 degrees C. for a duration ranging from 25 minutes to a few hours, and with a relative humidity above or about 25%. This will produce a certain amount of crosslinking depending on the characteristics of the freeze dried chitosan, which further depends on the concentration and/or molecular weight of chitosan in the solution as well as any additional components in the solution and on the freeze drying parameters. The degree of crosslinking that is obtained can be decreased or increased by modulating the temperature, duration, pressure, and/or relative humidity.

In one embodiment, the curing procedure can be conducted by placing the freeze dried chitosan having a desired amount of water into a water, steam and/or other liquid or vapor impervious pouch of a desired relative humidity that is sealed and then heated for a desired duration at a desired temperature until reaching a desired degree of crosslinking. The pouch can be made of most polymers that are utilized in standard packaging techniques for medical devices, such as polyolefins, polystyrenes, polycarbonates, and the like. After the freeze dried chitosan is placed in the pouch, the pouch is sealed so as to be at least substantially airtight. The sealed pouch is then subjected to heat and temperatures commensurate with the operation of an autoclave and for similar durations. The relative humidity inside the pouch can be controlled by controlling the amount of water in the chitosan, where the water can be provided by the plasticizer, humectant, or other hygroscopic substances within the pouch. Also, water can be added to the chitosan prior to sealing the pouch. The desired degree of crosslinking can be obtained by modulating the same parameters as described in connection with the autoclave process.

In one embodiment, the curing procedure can be performed with any system/equipment that can heat the chitosan to a desired temperature for a desired duration in the presence of water vapor. This can include placing the chitosan composition over a steamer or boiling water such that the temperature and relative humidity can be obtained.

In one embodiment, the curing process can be performed so as to heat the chitosan to a temperature from about 50 degrees C. to about 130 degrees C., more preferably from about 60 degrees C. to about 115 degrees C., and most preferably from about 70 degrees C. to about 100 degrees C. Also, the curing process can be performed from about 10 minutes to about 8 hours, more preferably from about 20 minutes to about 4 hours, and most preferably from about 30 minutes to about 1 hour. Additionally, the curing process can be performed at a relative humidity that equivalent to at or above about 30% relative humidity, more preferably above about 40%, and most preferably above about 50% and less than about 100% relative humidity at room temperature. The relative humidity can be achieved at room temperature and then the environment having the chitosan composition can be sealed or maintained so that no water is allowed to enter or exit the environment. The environment is then heated to the desired temperature to induce curing. During the curing process or temperature increase, the relative humidity will change; however, the water content will stay approximately the same. As such, the relative humidity is expressed as the relative humidity at room temperature.

Figure 3:
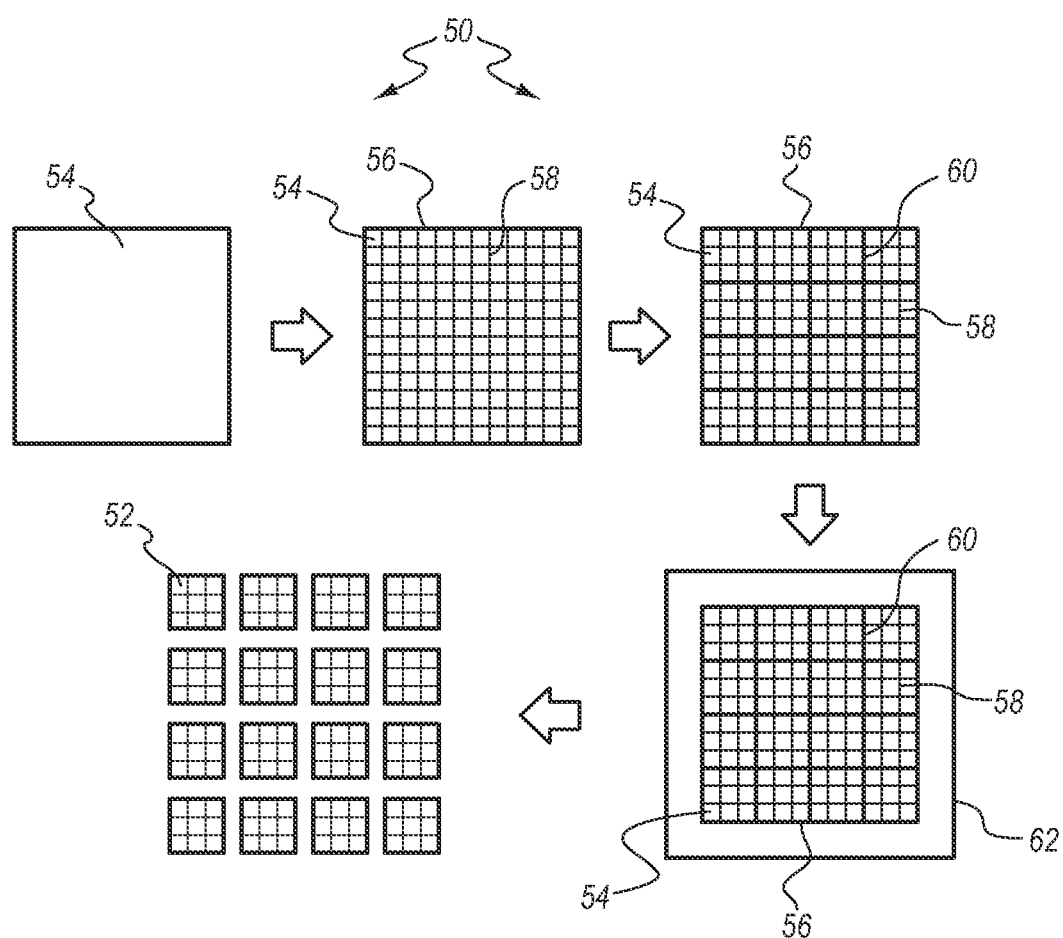
FIG. 3 is a schematic diagram that illustrates a process for preparing a structurally reinforced, stable chitosan hemostatic product in accordance with the present invention.
Figure 4A:
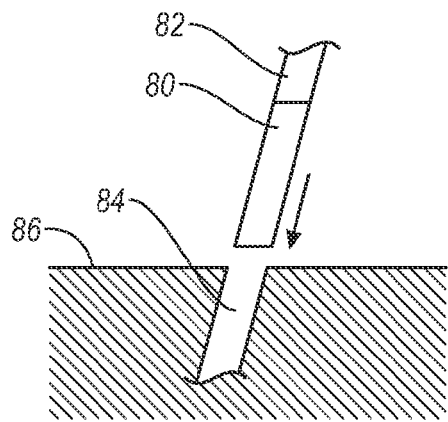
FIGS. 4A-4D include schematic diagrams of a process for delivering an implantable chitosan plug into an incision.
Figure 4B:
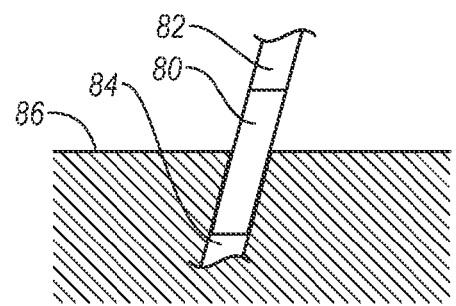
Figure 4C:
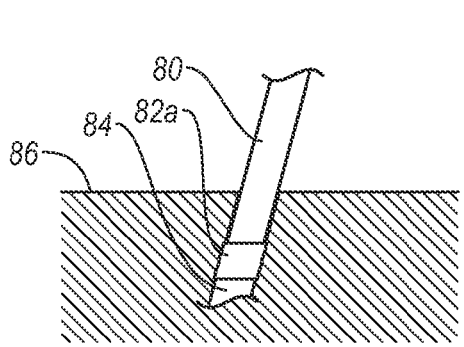
Figure 4D:
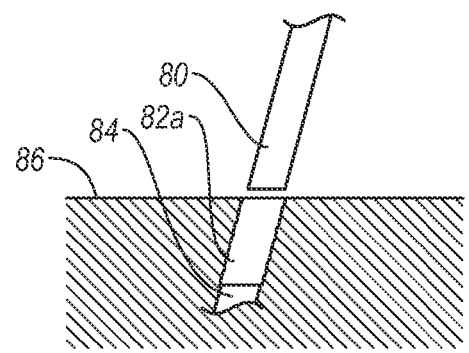

In one embodiment, the present invention includes an economical manufacturing process 50 for preparing a hemostatic chitosan plug 52 from a larger sheet of chitosan 54, which is illustrated in FIG. 3. Generally, the method includes casting an aqueous chitosan solution into a large sheet 54, which is then cut into the desired size of the plug 52. The chitosan having the desired molecular weight and characteristics can be placed into an aqueous solution, and the solution is then frozen solid before being subjected to a vacuum so as to freeze dry the chitosan. During this process, the solution is dispensed into a substantially flat tray 56 at a desired thickness, and the tray is optionally shimmied to settle the chitosan and solution and for obtaining a substantially uniform thickness. Optionally, a webbing, foam, mesh, or backing material 58 (e.g., biodegradable) is placed on the top of the solution so as to cover a portion or the entire surface area of the solution in the flat tray 56 or onto the dried chitosan after being freeze dried. A grate 60 having a mesh size commensurate with the desired size of the plug or other type of cutting apparatus is then employed to cut the large sheet 54 into individual plugs 52. The grate 60 is lowered into the solution or into the dried chitosan (e.g., large sheet 54) so as to define the size of the plugs. In the instance the grate 60 is used with the chitosan solution (as shown), it is placed into the solution on top of the webbing 58 so as to submerge the webbing to a desired depth. Once the grate 60 is lowered into the chitosan solution, the grate 60 and webbing 58 in combination with the viscosity of the chitosan solution reduce the risk of the solution flowing to one side of the tray if it is not kept exactly horizontal. This size of the mesh of the grate 60 can be used to divide the sheet into the desired size of plugs 52.

After preparation of the chitosan solution and placement of the grate 60, the entire assembly is processed with equipment 62 that freezes the tray 56 and grate 60 of the large sheet 54 using standard freezing equipment and techniques, and then freeze dried under vacuum using standard vacuum equipment and techniques. After freeze drying, the grate 60 is lowered all the way down into the dried chitosan until reaching the flat tray bottom 56, which cuts the chitosan into individual plugs 52 commensurate with the size and shape of the individual openings in the grate. In some instances, the plugs may stick to the grate after cutting. The individual plugs can then be pushed out of the grate by use of a poker or a plurality of pokers (not shown). Also, a waffle-shaped plate can be used to push the plugs from the grate. Optionally, the grate and/or flat tray can be coated with a non-stick coating, such as Teflon other similar polymers, ceramics, and the like. Additionally, the tray 56 can be designed to be covered, turned on it side, and attached to a hopper of an automated packaging system (not shown) that can retrieve the individual plugs 52 for packaging.

The use of a webbing, backing, or other similarly functional structurally reinforcing member can be utilized to increase the stability of the porous chitosan composition that is obtained from freeze drying. The general effectiveness of the chitosan hemostatic composition can be improved by increasing the total amount of surface area available to contact blood. While the porous chitosan hemostatic composition obtained from freeze drying can be more flexible than the solid sheets obtained from heat drying, the degree of freeze drying may result in a structure that can be supplemented with a structural member for improved functionality. The structural member can be a webbing, foam, mesh, backing material (e.g., biodegradable), fibers, fiber rebar, linearly disposed fibers, longitudinally disposed fibers, latitudinally disposed fibers, offset fibers, continuous fibers, combinations thereof, and the like. Additionally, the webbing can be configured as described above. The inclusion of a structurally reinforcing member can also provide a scaffold for the porous chitosan composition, and thereby increase the available surface area for contacting blood. Optionally, the structurally reinforcing member can also have hemostatic properties.

The hygroscopic characteristic of chitosan with or without the components that promote flexibility can also be utilized to provide flexibility. However, the hygroscopic components that are included in the chitosan plug can be used to attract water to induce flexibility. By controlling the amount and type of hygroscopic additives in the chitosan composition, the flexibility of the plug can be controlled. Additionally, controlling the relative humidity, water content, and hygroscopic components at the time of packaging, as well as controlling the water permeability of the packaging, the flexibility of the plug can be configured as desired for an end product use. That is, the flexibility can be controlled for specific applications of the chitosan hemostatic composition. For example, a plug having sufficient hygroscopic components can include an occlusive or semi-occlusive backing on the side opposite from the skin-contacting side such that the plug can absorb moisture from the skin and become softer and more flexible over time.

Increased flexibility can also be achieved for the chitosan hemostatic composition by inhibiting crystallization of chitosan. It is known that certain processing steps can produce crystalline and microcrystalline chitosan. However, the inhibition of such crystallization of chitosan can be controlled by controlling the processes involving chitosan so as to increase flexibility. One method for inhibiting crystallization is to include an effective amount of acidic counterions based on organic acids. As such, the same organic acids that provide flexibility, as described above, can also be utilized to inhibit crystallization. Accordingly, higher organic acids with residues larger than that of acetic acid are more beneficial for inhibiting crystallization.

In one embodiment, the hemostatic chitosan composition can be prepared into a high-density foam. Various processing techniques can be used to foam compositions. One advantageous method for preparing a high-density chitosan foam is the use of supercritical fluid foaming. Chitosan can be dissolved or absorbed into various supercritical fluids. An example is $CO_2$. After the chitosan is disposed in the supercritical fluid, the conditions causing the fluid to be supercritical (e.g., increased pressure, etc.) are removed and the supercritical fluid becomes a gas thereby puffing the chitosan into a high density foam. For example, releasing the pressure can cause pores to form in the chitosan, and the pore size and amount can be controlled by controlling the release of the gas. Thus, degassing a supercritical fluid containing chitosan can be used to puff the chitosan into a cake or sponge and form pores therein.

In one embodiment, the hydrophilic properties of chitosan can be utilized to produce a high-density foam. A chitosan solution can be prepared into a dense film that is then allowed to swell in an aqueous solution or in an atmosphere with adequate relative humidity. Also, the water can be provided by humectants or hygroscopic substances included with the chitosan. The water content of the film can be controlled in this manner, and the film can then be freeze dried under desired conditions to obtain a cake or sponge having the desired porosity and surface area. The characteristics of the chitosan film prior and during freeze drying can be modulated so as to control the porosity and surface area of chitosan available for performing the hemostatic function. Also, the chitosan can be prepared into a hydrogel that is freeze dried in order to provide desired structural characteristics as well as porosity and surface area. Additionally, the pre-swelling of the chitosan film for hydration and solvation prior to lyophilization or supercritical fluid foaming.

In one embodiment, the present invention includes a method of preparing a chitosan hemostatic product as follows: preparing an aqueous chitosan solution optionally containing a plasticizer, counterion, organic acid, multifunctional organic acid, or combinations thereof; dispensing the chitosan solution into a tray; incorporating a biocompatible, structurally reinforcing structure, such as a biodegradable webbing or rebar, into the chitosan solution; rapidly freezing the chitosan solution; placing the frozen chitosan under vacuum; vaporizing water from the chitosan to produce a dry or substantially dry chitosan composition; curing the chitosan composition so as to crosslink at least a portion of the chitosan polymers together; cutting the chitosan to the desired size of the desired product; packaging the chitosan; and sterilizing the chitosan.

In one embodiment, the method of preparing a chitosan hemostatic product as follows: solubilizing a low molecular weight of chitosan; freeze drying the chitosan; and curing the chitosan so as to crosslink the chitosan.

As shown in FIGS. 4A-4D, the hemostatic compositions of the present invention can be formulated into a tissue plug 80. This self anchoring device can be used to deliver the hemostatic chitosan composition 82 to provide hemostatis to a wound 84 in a tissue 86. The chitosan composition 82 can be configured and processed into a elongated cylindrical shape, and may anchor itself in the wound 84. The chitosan 82a may be in the form of a plug. Also, the plug 82a can be configured to allow a minimal or defined amount of entrance of body fluid with or without blood cells into the polymer network. Blood cells can be trapped by the polymer network. Such entrapment of blood cells can occlude blood from flowing further into or through the plug 82 and can help maintain structural integrity during use. Also, the total exclusion of blood cells can be beneficial by forming the occlusion on the outside of the device. The plug 82 can be biodegradable so as to degrade and disappear over time.

In one embodiment, the hemostatic compositions of the present invention can be used for hemostasis in a wound. The wound can be any type of internal wound that induces blood to flow from the wound. The chitosan product can be in the form of a sheet, block, cube, cylinder, sphere, irregular, combinations thereof and the like. The chitosan product is placed into the wound with or without pressure so that the blood interacts with the chitosan and agglutinates and coagulates.

Accordingly, the chitosan hemostatic composition can be prepared into a variety of implantable medical devices in various shapes and sizes so as to be usable for inhibiting blood flow and ooze from substantially any type of internal bleeding site. For example, the chitosan hemostatic composition can be prepared into implantable gauze pads, bandages, dressings, tissue fillers, fistula plugs, wound plugs, incision plugs, arteriotomy plugs, sealers, sheets, rolls, combinations thereof, and the like.

Additionally, the chitosan hemostatic compositions can be configured to inhibit inflammation. In some instances, the use of a foreign material as an implant or as a surface wound dressing can cause inflammation. For example, collagen-based systems can cause excessive inflammation. As such, chitosan may induce some inflammation, even if it is minor. In order to inhibit inflammation, the chitosan hemostatic composition can include an anti-inflammatory agent. The amount of anti-inflammatory agent to be included in the composition can be sufficient to treat, inhibit, or prevent inflammation at the site the chitosan is employed. Examples of anti-inflammatory agents can include non-steroidal anti-inflammatory drugs (NSAIDs), water-soluble anti-inflammatory agents, steroidal anti-inflammatory agents, and the like.

Examples of NSAIDs include aspirin, choline and magnesium salicylates, celecoxib, diclofenac potassium and sodium, diflunisal, etodolac, fenoprofen, flurbiprofen, ibuprofen, indomethacin, ketoprofen, meclofenamate sodium, mefanamic acid, meloxicam, nabumetone, naproxen, oxaprozin, piroxicam, rofecoxib, salsalate, sulindac, tolmetin sodium, valdexocib, and the like. Examples of steroidal anti-inflammatory agents include glucocorticoids, hydrocortisone, dexamethason, clobetasol, and the like.

Any pharmaceutical drug can be included in the chitosan hemostatic composition.

Figure 5A:
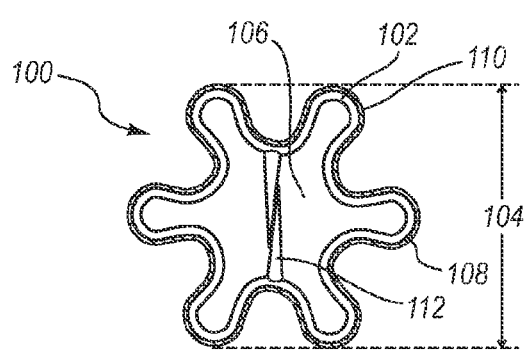
FIGS. 5A-5C illustrate an embodiment of a medical device having a coating of a chitosan hemostatic composition.
Figure 5B:
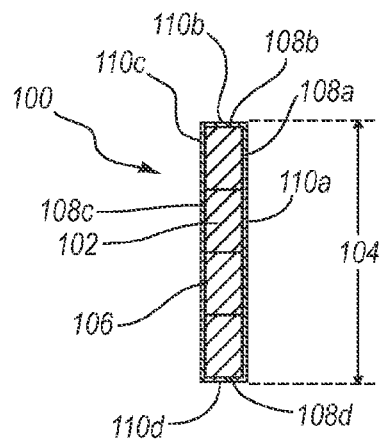
Figure 5C:
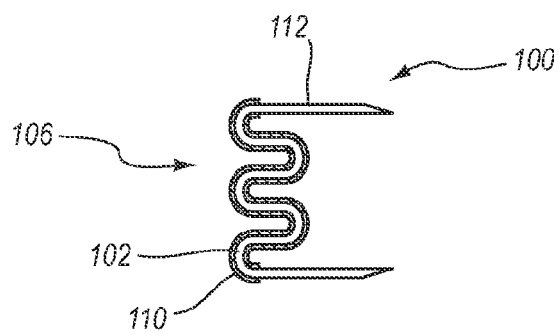

Additionally, the chitosan composition described herein can be applied to a medical device to provide the hemostatic effect. Any type of medical device can be coated with the chitosan composition. However, it can be beneficial for the chitosan coating to be on a medical device or portion of a medical device that does not enter into a blood vessel. Examples of medical devices that can include all or a portion thereof being coated with the chitosan composition can include a vessel closure element, a surgical clip, a staple, a suture device (e.g., suture needle), a suture, A closure element 100 has a body 102 that can have a natural, planar configuration with opposing tines 512 and a natural cross-section 104 as shown in FIG. 5A. The body 102 defines an aperture 106. FIG. 5A shows the closure element body 102 having a chitosan coating 110 thereon. FIG. 5B shows that the closure element 100 can have different portions or surfaces 108a-d to receive the chitosan composition. As shown, the first surface 108a may or may not have a first chitosan coating 110a, the second surface 108b may or may not have a second chitosan coating 110b, the third surface 108c may or may not have a third chitosan coating 110c, and the fourth surface 108d may or may not have a fourth chitosan coating 110d. Also, opposing sides may have one side (e.g., 108b) with the chitosan coating while the opposing side (e.g., 108a) is devoid of the chitosan coating. As shown in FIG. 5C, by rotating the opposing tines 112 axially, the closure element 100 can be deformed to form a substantially tubular shape. The tubular shape shows the chitosan coating 110 to be located on the body 102, but not on the tines 112. The tines 112 being devoid of having the chitosan composition can inhibit chitosan from entering into the blood stream during a vessel closure procedure. The coating can be applied by spraying, painting, depositing, dipping, or other technique for applying a coating onto an object. Various other medical devices can be similarly coated with chitosan.

EXAMPLES

Example 1

A chitosan solution is prepared by introducing 13.5 grams of chitosan with a viscosity of 11 cps (reported as a 1% chitosan solution in 1% acetic acid) into a water, lactic acid, and PEG 200 solution. The PEG 200 being present at a concentration of 5.3%, the lactic acid being present at a concentration of 5.0%, and the chitosan reaching a concentration of 7.4% w/w in the solution. The solution is poured into aluminum trays to a height of about 1.5-2 mm, and strips of 2 cm wide biodegradable webbing are embedded in the solution. The chitosan solution is then frozen by being introduced into a freezing apparatus having a shelf temperature of −40 degrees C. The frozen chitosan composition is then subjected to vacuum at approximately 10 mTorr for a duration of 24 hours until obtaining a substantially dried chitosan composition. The resulting chitosan product is cut in the shape of a square having dimensions of approximately 40.0 mm (width), 40.0 mm (length), and 1.2 mm (thickness).

The dried chitosan is introduced into a package made of foil LDPE peelable laminate, sealed, and subjected to a relative humidity of 30 or 50%, for a duration of 8, 4, 2 or 1 hour. The effectiveness of the cross-linking can be investigated by extracting the crosslinked plugs with water and measuring the amount of extractable chitosan as a percentage of the total amount of chitosan.

The results as expected are represented in the table below:

| Cross-linking conditions | Percent chitosan extractable after crosslinking |
| --- | --- |
| 50% RH, 8 hrs, 90 C. | about 6 |
| 50% RH, 4 hrs, 90 C. | about 9 |
| 50% RH, 2 hrs, 90 C. | about 12 |
| 50% RH, 1 hr, 90 C. | about 21 |
| 30% RH, 8 hrs, 90 C. | about 15 |
| 30% RH, 1 hr, 90 C. | about 28 |

Example 2

A chitosan solution is prepared by introducing 13.5 grams of chitosan with a viscosity of 11 cps (reported as a 1% chitosan solution in 1% acetic acid) into a water, lactic acid, and PEG 200 solution. The PEG 200 being present at a concentration of 5.3%, the lactic acid being present at a concentration of 5.0%, and the chitosan reaching a concentration of 7.4% w/w in the solution. The solution is poured into aluminum trays to a height of about 1.5-2 mm.

The chitosan solution is then frozen by being introduced into a freezing apparatus having a shelf temperature of −40 degrees C. The frozen chitosan composition is then subjected to vacuum at approximately 10 mTorr for a duration of 24 hours until obtaining a substantially dried chitosan composition. The resulting chitosan product is cut in the shape of a square having dimensions of approximately 40.0 mm (width), 40.0 mm (length), and 1.2 mm (thickness). The dried chitosan is then introduced into a package made of foil LDPE peelable laminate, sealed, and subjected to heat at a temperature of 90 degrees C. for one hour. The relative humidity in the sealed package is about 50 percent. The chitosan product is effective at stopping bleeding within 5 minutes of venous bleeding in an aggressively anti-coagulated porcine model.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of preparing a stable chitosan hemostatic implant, the method comprising:
    preparing a non-aqueous lyophilizable solution of chitosan polymers;
    freezing the non-aqueous solution to obtain a frozen chitosan composition;
    placing the frozen chitosan composition under vacuum so as to dry the chitosan composition; and
    curing the dried chitosan composition by first exposing the dried chitosan to a relative humidity and then curing the dried chitosan composition under heat so as to crosslink the chitosan polymers.

2. The method as in claim 1, wherein the chitosan polymers have an average molecular weight less than about 600 kD.

3. The method as in claim 1, further comprising
    placing the lyophilizable non-aqueous solution into a mold having a shape; and
    freezing the lyophilizable non-aqueous solution in the mold such that the dried chitosan composition forms in the shape of the mold.

4. The method as in claim 1, further comprising:
    placing a biodegradable structurally reinforcing member into the lyophilizable solution prior to freezing.

5. The method as in claim 4, further comprising:
    introducing the lyophilizable non-aqueous solution into a tray;
    inserting a cutting member into the lyophilizable solution in the tray, the cutting member being configured to cut the dried chitosan composition into a plurality of chitosan hemostatic products;
    freeze drying the chitosan composition in the tray with the cutting member; and
    cutting the freeze dried chitosan composition into the plurality of chitosan hemostatic products.

6. The method as in claim 1, wherein the cooling and/or freezing is at a rate of more than or about 1° C./minute and/or the cooling and/or freezing is at a temperature of less than or about −40 degrees C.

7. The method as in claim 1, wherein the curing crosslinks at least about 50% of the chitosan polymers.

8. The method as in claim 7, wherein the curing is at a temperature between about 50 degrees C. to about 130 degrees C.

9. The method as in claim 8, wherein exposing the dried chitosan further comprises exposing the chitosan to a relative humidity of about 30% at room temperature.

10. The method as in claim 8, wherein the curing is for about 10 minutes to about 8 hours.

11. The method as in claim 10, wherein the curing is conducted in an autoclave.

12. The method as in claim 7, further comprising:
    placing the dried chitosan into a gas-impermeable pouch;
    sealing the pouch; and
    curing the chitosan within the pouch.

13. The method as in claim 1, further comprising sterilizing the crosslinked chitosan hemostatic product.

14. The method as in claim 13, further comprising introducing a free radical scavenger into the lyophilizable solution in an amount sufficient to inhibit degradation of chitosan.

15. The method as in claim 13, wherein the sterilization is by gamma radiation.

16. The method as in claim 1, wherein the chitosan hemostatic product is prepared without mechanically compressing the dried chitosan to increase density.

17. The method as in claim 1, wherein the chitosan hemostatic product is prepared without processing the dried chitosan in a manner that induces the formation of cracks or microcracks that provide flexibility when dry.

18. The method as in claim 1, further comprising configuring the chitosan hemostatic product into an implantable plug.

19. The method as in claim 1, further comprising configuring the chitosan hemostatic product to be capable of being inserted into a tissue.

20. A method of preparing a stable chitosan hemostatic implant, the method comprising:
    preparing a non-aqueous lyophilizable solution of chitosan polymers and a non-volatile plasticizer, wherein the chitosan polymers have an average molecular weight less than about 600 kD, the lyophilizable non-aqueous solution has a chitosan concentration between about 2% to about 20%, and the plasticizer is lactic acid or an equally or less volatile organic acid;

rapidly freezing the solution to obtain a frozen chitosan composition, wherein the cooling and/or freezing is at a rate of more than or about 1° C./minute and/or the cooling and/or freezing is conducted at a temperature of less than or about −40 degrees C.;

placing the frozen chitosan composition under vacuum so as to substantially dry the chitosan composition; and curing the dried chitosan composition under heat and at a relative humidity so as to crosslink at least about 25% of the chitosan polymers, wherein the curing is performed at a temperature between about 50 degrees C. to about 130 degrees C., the curing is performed after a moisture level is obtained by exposing the chitosan to a relative humidity of about 30% at room temperature, and the curing is performed for about 10 minutes to about 8 hours.

21. The method as in claim 20, wherein the lyophilizable non-aqueous solution is pre-evaporated prior to being frozen so as to increase the chitosan concentration that is frozen by at least about 10%.

22. The method as in claim 20, further comprising:
placing the dried chitosan into a gas-impermeable pouch;
sealing the pouch; and
curing the chitosan within the pouch.

23. The method as in claim 20, further comprising sterilizing the crosslinked chitosan hemostatic product with gamma radiation.

24. The method as in claim 20, wherein the chitosan hemostatic product is prepared without mechanically compressing the dried chitosan to increase density and/or the chitosan hemostatic product is prepared without processing the dried chitosan in order to induce the formation of cracks or microcracks that provide flexibility when dry.

25. A method as in claim 20, further comprising
placing the lyophilizable non-aqueous solution into a mold having a shape; and
freezing the lyophilizable solution in the mold such that the dried chitosan composition forms in the shape of the mold.

* * * * *